United States Patent [19]
Shimasaki et al.

[11] Patent Number: 5,773,669
[45] Date of Patent: Jun. 30, 1998

[54] PROCESS FOR PRODUCTION OF VINYL ETHER

[75] Inventors: Yuuji Shimasaki, Otsu; Akira Kurusu, Kyoto, both of Japan

[73] Assignee: Nippon Shokubai Co., Ltd., Osaka, Japan

[21] Appl. No.: 816,026

[22] Filed: Mar. 11, 1997

[30] Foreign Application Priority Data

Mar. 12, 1996 [JP] Japan ..................................... 8-054515

[51] Int. Cl.$^6$ .................................................. C07C 41/00
[52] U.S. Cl. ......................... 568/687; 568/698; 502/240; 502/243; 502/250; 502/341
[58] Field of Search ..................................... 568/687, 698; 502/240, 243, 250, 341

[56] References Cited

FOREIGN PATENT DOCUMENTS

| | | |
|---|---|---|
| 0227461 | 7/1987 | European Pat. Off. . |
| 0228898 | 7/1987 | European Pat. Off. . |
| 0701986 | 3/1996 | European Pat. Off. . |
| 1735264 | 5/1992 | U.S.S.R. . |

OTHER PUBLICATIONS

Canadian Journal of Chemical Engineering, vol. 55, No. 3, Jun. 1977, pp. 341–346, J.C. Salazar–Tello et al., "Etude de la déshydratation des ethers de glycol comme une novelle voie de synthèse des vinyl–ethers".

Andersson et al; Journal of Organic Chemistry; 55, 5757–5761, 1990.

*Primary Examiner*—Gary Geist
*Assistant Examiner*—Sreeni Padmanabhan
*Attorney, Agent, or Firm*—Sherman and Shalloway

[57] ABSTRACT

There is provided a simple and rational process for production of a vinyl ether, which comprises subjecting a 2-hydroxyalkoxy compound having, in the molecule, at least one 2-hydroxyalkoxy group and at least one functional group selected from the group consisting of a hydroxyl group and an amino group, to an intramolecular dehydration reaction in a gas phase to convert the compound into a corresponding functional group-containing vinyl ether in one step without using any subsidiary raw material or any solvent. The process is characterized by using, as a catalyst, an oxide containing an alkali metal element and/or an alkaline earth metal element and silicon.

7 Claims, No Drawings

PROCESS FOR PRODUCTION OF VINYL ETHER

The present invention relates to a process for producing a functional group-containing vinyl ether in one step by subjecting the 2-hydroxyalkyl group of a 2-hydroxyalkoxy compound containing at least one 2-hydroxyalkoxy group and at least one functional group, to an intramolecular dehydration reaction in a gas phase; as well as to a catalyst used in the process.

The functional group-containing vinyl ether produced by the process of the present invention is useful as a raw material for polymers, coatings, organic synthetics, etc.

The technique for producing a functional group-containing vinyl ether in one step by subjecting the 2-hydroxyalkyl group of a 2-hydroxyalkoxy compound having at least one 2-hydroxyalkoxy group and at least one functional group, to an intramolecular dehydration reaction in a gas phase, is a novel technique developed by the present invention.

As to the conversion of the 2-hydroxyalkoxy group of a 2-hydroxyalkoxy compound into a vinyl ether group by dehydration, there are prior techniques. These techniques employ indirect dehydration which comprises converting a glycol ether into an ester type intermediate and then decomposing the intermediate to obtain an alkyl vinyl ether. For example, Can. J. Chem. Eng., 1977, Vol. 55, No. 3, pp. 341–346 describes a process which comprises reacting a glycol ether and acetic anhydride in the presence of zinc chloride (a catalyst) to synthesize an ester and heat-decomposing the ester in a gas phase to form an alkyl vinyl ether and acetic acid. This process, however, have problems, for example, in that acetic anhydride is required in an amount of one equivalent per one equivalent of the glycol ether and, therefore, acetic acid is formed as a by-product in an amount of one equivalent per one equivalent of the alkyl vinyl ether (a product). These problems make difficult the industrial use of the process.

Also, SU 1735264 A1 discloses a liquid-phase indirect dehydration process, i.e. a process which comprises reacting a glycol ether with potassium hydroxide (KOH) and potassium hydrogensulfate ($KHSO_4$) each of an amount of one equivalent or more per one equivalent of the glycol ether, in an aqueous solution. In this process, first the glycol ether and $KHSO_4$ are reacted to form an sulfuric acid ester and then the ester is reacted with KOH to be decomposed into an alkyl vinyl ether and $K_2SO_4$. This process, however, requires subsidiary raw materials each of an amount of one equivalent or more per one equivalent of the glycol ether and, moreover, generates a large amount of a waste solution and a large amount of an inorganic salt ($K_2SO_4$); therefore, is low in productivity and economy; and makes difficult the industrial use.

Currently, alkyl vinyl ethers are in production by a high-pressure addition reaction of acetylene and an alcohol, known as the Reppe process. When in this reaction, a functional group-containing alcohol is used as the alcohol, a functional group-containing vinyl ether may be produced. Such a process, however, involves a problem of complicated reaction control because acetylene may give rise to decomposition and explosion at a high pressure.

One object of the present invention is to provide a simple and rational process for production of a vinyl ether, which comprises subjecting the 2-hydroxyalkyl group of a 2-hydroxyalkoxy compound having at least one 2-hydroxyalkoxy group and at least one functional group, to an intramolecular dehydration reaction in a gas phase to convert the compound into a corresponding functional group-containing vinyl ether in one step without using any subsidiary raw material or any solvent.

Another object of the present invention is to provide a catalyst effectively used in such a process for production of a vinyl ether.

In order to achieve the above objects and alleviate the above-mentioned problems of the prior art, the present inventors made a study on a catalyst capable of subjecting the 2-hydroxyalkyl group of a 2-hydroxyalkoxy compound having at least one 2-hydroxyalkoxy group and at least one functional group, to a dehydration reaction in a gas phase in one step. As a result, the present inventors found out that (1) the intended reaction proceeds stably at a high selectivity over a long period of time when an oxide catalyst containing an alkali metal element and/or an alkaline earth metal element and silicon is used and (2) when a compound having two 2-hydroxyalkoxy groups is used as the raw material, there can be produced not only a vinyl ether having a mono(2-hydroxyalkoxy) group but also a divinyl ether.

According to the present invention, there is provided a process for producing a vinyl ether, which comprises subjecting a 2-hydroxyalkoxy compound having, in the molecule, at least one 2-hydroxyalkoxy group and at least one functional group selected from the group consisting of a hydroxyl group and an amino group, to an intramolecular dehydration reaction in a gas phase in the presence of an oxide catalyst containing an alkali metal element and/or an alkaline earth metal element and silicon, to convert the 2-hydroxyalkoxy group partially or completely to a vinyl ether group to obtain a corresponding vinyl ether.

According to the present invention, there is also provided, as a catalyst effective in the above process, an oxide containing an alkali metal element and/or an alkaline earth metal element and silicon.

In the present process, the 2-hydroxyalkyl group of a 2-hydroxyalkoxy compound having, in the molecule, at least one 2-hydroxyalkoxy group and at least one functional group selected from the group consisting of a hydroxyl group and an amino group, is subjected to an intramolecular dehydration reaction in a gas phase in the presence of an oxide catalyst to produce a functional group-containing vinyl ether. The reaction is represented, for example, by the following general formula (4):

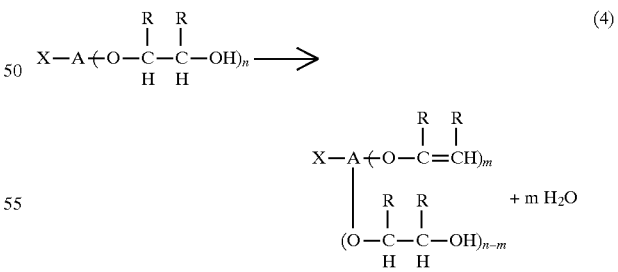

[wherein n, X, A and Rs have the same definitions as given in a general formula (1) (shown below), and m is 1 or 2 with a proviso that when n is 1, m is 1].

The 2-hydroxyalkoxy compound as a raw material needs to have such a vapor pressure that it can be fed into the catalyst layer in a gas form under the reaction conditions, and is preferably a compound represented by the following general formula (1):

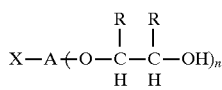

(1)

(wherein n is 1 or 2; X is a hydrogen atom, a hydroxyl group or a dialkylamino group with a proviso that when n is 1, X is not a hydrogen atom; A is at least one group selected from a straight-chain or branched chain alkyl group, a cycloalkyl group, an aryl group, an aralkyl group and an alkoxy group; and Rs are each independently a group selected from a hydrogen atom and a hydrocarbon group of 1–6 carbon atoms). The 2-hydroxyalkoxy compound can be exemplified by (a) diethylene glycol, (b) triethylene glycol, (c) diisopropylene glycol, (d) 2-(3-hydroxypropoxy)ethanol, (e) 2-(4-hydroxybutoxy)ethanol and (f) 2-(2-dimethylaminoethoxy) ethanol, but is not restricted thereto.

From each of the above 2-hydroxyalkoxy compounds of general formula (1) can be produced, according to the present process, corresponding vinyl ethers represented by the following general formula (2):

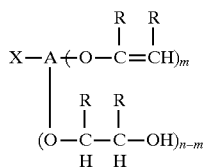

(2)

(wherein n, X, A and Rs have the same definitions as given in the general formula (1); and m is 1 or 2 with a proviso that when n is 1, m is 1). That is, from the raw materials (a) to (f) mentioned above can be produced (a') hydroxyethyl vinyl ether, (b') hydroxyethoxyethyl vinyl ether, (c') 1-(2-hydroxypropoxy)-1-propylene, (d') hydroxypropyl vinyl ether, (e') hydroxybutyl vinyl ether and (f') dimethylaminoethyl vinyl ether, respectively.

When the raw material, 2-hydroxyalkoxy compound, has two 2-hydroxyalkyl groups, it is possible to produce a divinyl ether. For example, from the compounds pounds (a) and (b) can be produced (a") divinyl ether and (b") ethylene glycol divinyl ether, respectively. The proportion of the divinyl ether produced can be changed by varying the reaction conditions, and the proportion can be increased by elevating the reaction temperature or by decreasing the gas hourly space velocity (GHSV).

The 2-hydroxyalkoxy compound, which is a raw material in the present process, when subjected to a high-temperature gas-phase reaction in the presence of a strong acid catalyst (which is generally used in dehydration reactions), easily give rises to cleavage of the ether bond an/or reaction of the functional group and, as a result, gives substantially no intended product (functional group-containing vinyl ether). When the catalyst of the present invention is used, however, side reactions are suppressed; the gas-phase intramolecular dehydration reaction of 2-hydroxyethyl group proceeds selectively; and a functional group-containing vinyl ether can be produced at a very high yield.

The catalyst of the present invention is very effective in carrying out the reaction of general formula (4) in a gas phase.

The catalyst of the present invention has features that the activity is not reduced substantially even when the catalyst is used in a long-term continuous reaction and, even when the catalyst is deteriorated by coking, etc., the activity is restored by passage of air through the catalyst layer and combustion of the coke formed.

The catalyst of the present invention is an oxide containing an alkali metal element and/or an alkaline earth metal element and silicon, and is preferably an oxide represented by the following general formula (3):

$$M_aSi_bY_cO_d \quad (3)$$

(wherein M is at least one element selected from alkali metal elements and alkaline earth metal elements; Si is silicon; Y is at least one element selected from the group consisting of B, Al and P; O is oxygen; and a, b, c and d are the atom numbers of M, Si, Y and O, respectively, with provisos that when a=1, b is 1–500 and c is 0–1 and d is a value determined by the values of a, b and c and the bonding states of individual constituent elements).

In the catalyst of the general formula (3), the proportion of silicon to M (which is at least one element selected from alkali metal elements and alkaline earth metal elements) is 1–500, preferably 5–200 in terms of atomic ratio.

The proportion of Y as optional component (which is at least one element selected from the group consisting of B, Al and P) to M is generally appropriate to be 0–1 in terms of atomic ratio, although it varies depending upon the kind of M and the proportion of Si.

The catalyst of the present invention has no particular restriction as to the production process and can be produced by any known process. With respect to the alkali metal element and/or the alkaline earth metal element, which is an essential element of the present catalyst, the raw material thereof can be an oxide, a hydroxide, a halide, a salt (e.g. carbonate, nitrate, carboxylate, phosphate or sulfate), a metal or the like. With respect to silicon, which is another essential component, the raw material thereof can be silicon oxide, silicic acid, a silicic acid salt (e.g. alkali metal silicate or alkaline earth metal silicate), a silicon-containing molecular sieve (e.g. aluminosilicate or silicoaluminophosphate), an organic silicic acid ester or the like. With respect to Y, which is an optional component, the raw material thereof can be an oxide, a hydroxide, a halide, a salt (e.g. carbonate, nitrate, carboxylate, phosphate or sulfate), a metal or the like.

The catalyst of the present invention can be produced, for example, by the following processes:

(1) a process which comprises dissolving or suspending an alkali metal element source and/or an alkaline earth metal element source and a silicon source in water, concentrating the solution or suspension with heating and stirring, drying the concentrate, molding the dried material, and calcinating the molding;

(2) a process which comprises immersing molded silicon oxide in an aqueous solution of an alkali metal element source and/or an alkaline earth metal element source, and subjecting the resulting material to concentration with heating, drying, and calcination;

(3) a process which comprises adding, to a silicic acid salt or a silicon-containing oxide, an aqueous solution of an alkali metal element source and/or an alkaline earth metal element source, and subjecting them to mixing, drying, molding and calcination; and (4) a process which comprises doping a silicon-containing molecular sieve with an alkali metal element source and/or an alkaline earth metal element source by ion exchange, and subjecting the doped molecular sieve to drying, molding and calcination.

In order to allow the catalyst to contain Y (an optional component), there may be used an alkali metal element source and/or an alkaline earth metal element source, at least either of which contains Y, or a silicon source containing Y; or, a raw material for Y may be added in the course of catalyst production.

The catalyst of the present invention may be used by being supported on a known carrier (e.g. alumina or silicon carbide) or being mixed therewith.

The calcination temperature employed in catalyst production is 300°–1,000° C., preferably 400°–800° C. although it varies depending upon the kinds of catalyst raw materials used.

In carrying out the present process, the reactor can be any of a fixed bed flow type and a fluidized bed type. The reaction is conducted at such a temperature and pressure that the raw material, i.e. a 2-hydroxyalkoxy compound can maintain a gaseous state. The reaction pressure is ordinarily atmospheric pressure or reduced pressure, but an applied pressure may be used as well. The reaction temperature is generally 300°–500° C., preferably 350°–450° C. although it varies depending upon the kind of raw material and other reaction conditions. When the reaction temperature is lower than 300° C., the conversion of the raw material is significantly low; when the reaction temperature is higher than 500° C., the selectivity of the vinyl ether (an intended product) is significantly low. In the reaction, the raw material is fed into the catalyst layer by diluting it with a substance inert to the reaction, such as nitrogen, helium, argon, hydrocarbon or the like and/or reducing the pressure of the system so that the partial pressure of the raw material becomes 5–600 mmHg. The gas hourly space velocity (GHSV) of the raw material is generally 1–1,000 h$^{-1}$, preferably 10–500 h$^{-1}$ although it varies depending upon the kind of the raw material and other reaction conditions.

The present invention is hereinafter described specifically by way of Examples. However, the present invention is in no way restricted to these Examples.

In the Examples, "conversion", "selectivity" and "per-pass yield" have the following definitions.

Conversion (mole %) =
[(moles of 2-hydroxyalkoxy compound consumed)/
(moles of 2-hydroxyalkoxy compound fed) × 100
Selectivity (mole %) =
[(moles of vinyl ether formed)/(moles of
2-hydroxyalkoxy compound consumed)] × 100
Per-pass yield (mole %) =
[(moles of vinyl ether formed/(moles of
2-hydroxyalkoxy compound fed) × 100

EXAMPLE 1

[Catalyst production]

30 g of a spherical silica gel (5–10 mesh) was immersed in a solution of 0.67 g of sodium hydroxide dissolved in 40 g of water, for 2 hours. The resulting material was concentrated on a hot water bath; the concentrate was dried in air at 120° C. for 20 hours; and the dried material was calcinated in air at 600° C. for 2 hours to obtain a catalyst having a composition of $Na_1Si_{30}$ in terms of atomic ratio when oxygen was excluded. [Reaction]

10 ml of the catalyst was filled in a stainless steel-made reaction tube having an inner diameter of 10 mm. Then, the reaction tube was immersed in a molten salt bath of 400° C., and a raw material gas consisting of diethylene glycol and nitrogen was fed into the reaction tube. In the raw material gas, diethylene glycol was diluted with nitrogen so that the partial pressure of diethylene glycol became 76 mmHg. A reaction was conducted at an atmospheric pressure while the space velocity of diethylene glycol was being maintained at 200 h$^{-1}$. After 1 hour from the start of the feeding, the reaction product was analyzed by gas chromatography. As a result, the conversion of diethylene glycol and the selectivity and per-pass yield of hydroxyethyl vinyl ether were 10 mole %, 95 mole % and 9.5 mole %, respectively.

EXAMPLE 2

[Catalyst production]

30 g of silicon oxide was added to a solution of 4.07 g of cesium carbonate dissolved in 40 g of water. The mixture was concentrated on a hot water bath with stirring. The concentrate was subjected to drying in air at 120° C. for 20 hours, crushing into 9–16 mesh, and calcined in air at 500° C. for 2 hours to obtain a catalyst having a composition of $Cs_1Si_{20}$ in terms of atomic ratio when oxygen was excluded.

[Reaction]

A reaction was conducted in the same manner as in Example 1 except that the catalyst was changed to the above catalyst and the reaction temperature was changed. When the reaction temperature was 370° C., after 1 hour from the start of the feeding, the conversion of diethylene glycol and the selectivity and per-pass yield of hydroxyethyl vinyl ether were 17 mole %, 89 mole % and 15 mole %, respectively. When the reaction temperature was increased to 430° C., the conversion of diethylene glycol and the selectivity and per-pass yield of hydroxyethyl vinyl ether were 60 mole %, 87 mole % and 52 mole %, respectively. When the reaction temperature was increased to an even higher temperature, i.e. 450° C. hydroxyethyl vinyl ether was formed at a selectivity and per-pass yield of 50 mole % and 35 mole%, respectively, at a diethylene glycol conversion of 70 mole %; and simultaneously therewith, divinyl ether was formed at a selectivity and per-pass yield of 10 mole % and 7 mole %, respectively.

EXAMPLE 3

[Catalyst production]

30 g of silicon oxide was added to a solution of 1.69 g of potassium nitrate dissolved in 40 g of water. The mixture was concentrated on a hot water bath with stirring. The concentrate was subjected to drying in air at 120° C. for 20 hours, crushing into 9–16 mesh, and calcined in air at 600° C. for 2 hours to obtain a catalyst having a composition of $K_1Si_{10}$ in terms of atomic ratio when oxygen was excluded.

[Reaction]

A reaction was conducted in the same manner as in Example 1 except that the catalyst was changed to the above catalyst and diethylene glycol was replaced by triethylene glycol. After 1 hour from the start of the feeing, the conversion of triethylene glycol and the selectivity and per-pass yield of hydroxyethoxyethyl vinyl ether were 30 mole %, 90 mole % and 27 mole %, respectively.

EXAMPLE 4

[Catalyst production]

A catalyst having a composition of $Rb_1Si_{10}$ in terms of atomic ratio when oxygen was excluded, was obtained in the same manner as in Example 3 except that 1.69 g of potassium nitrate was changed to 5.13 g of rubidium hydroxide.

[Reaction]

A reaction was conducted in the same manner as in Example 3 except that the catalyst was changed to the above catalyst and the reaction temperature was changed to 410° C. After 1 hour from the start of the feeding, the conversion of triethylene glycol and the selectivity and per-pass yield of hydroxyethoxyethyl vinyl ether were 25 mole %, 91 mole % and 23 mole %, respectively.

EXAMPLE 5

[Reaction]

A reaction was conducted in the same manner as in Example 3 except that the catalyst was changed to the catalyst of Example 2 and the reaction temperature was changed. When the reaction temperature was 370° C., after 1 hour from the start of the feeding, the conversion of triethylene glycol and the selectivity and per-pass yield of hydroxyethoxyethyl vinyl ether were 32 mole %, 97 mole % and 31 mole %, respectively. When the reaction temperature was increased to 400° C., hydroxyethoxyethyl vinyl ether was formed at a selectivity and per-pass yield of 84 mole % and 56 mole%, respectively, at a triethylene glycol conversion of 67 mole %; and simultaneously therewith, ethylene glycol divinyl ether was formed at a selectivity and per-pass yield of 4 mole % and 3 mole %, respectively. When the reaction temperature was increased to an even higher temperature, i.e. 430° C., hydroxyethoxyethyl vinyl ether was formed at a selectivity and per-pass yield of 32 mole % and 32 mole%, respectively, at a triethylene glycol conversion of 100 mole %; and simultaneously therewith, ethylene glycol divinyl ether was formed at a selectivity and per-pass yield of 26 mole % and 26 mole %, respectively.

EXAMPLE 6

[Reaction]

A reaction was conducted in the same manner as in Example 1 except that the catalyst was changed to the catalyst of Example 2, diethylene glycol was replaced by 2-(2-dimethylaminoethoxy)ethanol, and the reaction temperature was changed. When the reaction temperature was 340° C., after 1 hour from the start of the feeding, the conversion of 2-(2-dimethylaminoethoxy)ethanol and the selectivity and per-pass yield of 2-dimethylaminoethyl vinyl ether were 46 mole %, 45 mole % and 21 mole %, respectively. When the reaction temperature was increased to 370° C., the conversion of 2-(2-dimethylaminoethoxy) ethanol and the selectivity and per-pass yield of 2-dimethylaminoethyl vinyl ether were 90 mole %, 51 mole % and 46 mole %, respectively.

As demonstrated by the above Examples, according to the present process, by subjecting the 2-hydroxyalkyl group of a 2-hydroxyalkoxy compound (a raw material) having, in the molecule, at least one 2-hydroxyalkoxy group and at least one functional group selected from a hydroxyl group and an amino group, to an intramolecular reaction in a gas phase, there can be produced a corresponding functional group-containing vinyl ether in one step without using any subsidiary raw material or any solvent. When the raw material is a 2-hydroxyalkoxy compound having two 2-hydroxyalkoxy groups, not only a vinyl ether having a mono(2-hydroxyalkoxy) group but also a divinyl ether can be produced.

What is claimed is:

1. A process for producing a vinyl ether, which comprises subjecting a 2-hydroxyalkoxy compound having, in the molecule, at least one 2-hydroxyalkoxy group and at least one functional group selected from the group consisting of a hydroxyl group and an amino group, to an intramolecular dehydration reaction in a gas phase in the presence of an oxide catalyst containing an alkali metal element and/or an alkaline earth metal element and silicon, to convert the 2-hydroxyalkoxy group partially or completely to a vinyl ether group to obtain a corresponding vinyl ether.

2. A process according to Claim 1, wherein the 2-hydroxyalkoxy compound is a compound represented by the following general formula (1):

wherein n is 1 or 2; X is a hydrogen atom, a hydroxyl group or a dialkylamino group with a proviso that when n is 1, X is not a hydrogen atom; A is at least one group selected from a straight-chain or branched chain alkyl group, a cycloalkyl group, an aryl group, an aralkyl group and an alkoxy group; and Rs are each independently a group selected from a hydrogen atom and a hydrocarbon group of 1–6 carbon atoms, and the vinyl ether is a compound represented by the following general formula (2):

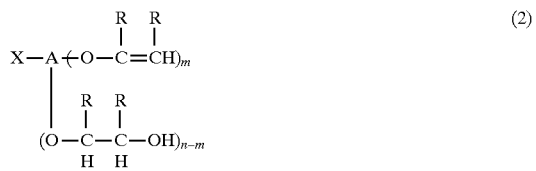

wherein n, X, A and Rs have the same definitions as given in the general formula (1); and m is 1 or 2 with a proviso that when n is 1, m is 1.

3. A process according to claim 1 or 2, wherein the catalyst is an oxide represented by the following general formula (3):

wherein M is at least one element selected from alkali metal elements and alkaline earth metal elements; Si is silicon; Y is at least one element selected from the group consisting of B, Al and P; O is oxygen; and a, b, c and d are the atom numbers of M, Si, Y and O, respectively, with provisos that when a=1, b is 1–500 and c is 0–1 and d is a value determined by the values of a, b and c and the bonding states of individual constituent elements.

4. A process for producing a vinyl ether, which comprises subjecting a 2-hydroxyalkoxy compound having, in the molecule, at least one 2-hydroxyalkoxy group and at least one functional group selected from the group consisting of a hydroxyl group and an amino group, to an intramolecular dehydration reaction in a gas phase at a temperature of 300° to 500° C. in the presence of an oxide catalyst represented by the following general formula (3):

wherein M is at least one element selected from alkali metal elements and alkaline earth metal elements; Si is silicon, Y is at least one element selected from the group consisting of B, Al and P; O is oxygen; and a, b, c, and d are the atom numbers of M, Si, Y and O, respectively, with provisos that when a=1, b is 1–500 and c is 0–1 and d is a value determined by the values of a, b and c and the bonding states of individual constituent elements, to convert the 2-hydroxyalkoxy group partially or completely to a vinyl ether group to obtain a corresponding vinyl ether.

5. A process according to claim 4, wherein the 2-hydroxyalkoxy compound is a compound represented by the following general formula (1):

$$X-A+O-\underset{H}{\overset{R}{\underset{|}{C}}}-\underset{H}{\overset{R}{\underset{|}{C}}}-OH)_n, \quad (1)$$

wherein n is 1 or 2; X is a hydrogen atom, a hydroxyl group or a dialkylamino group with a proviso that when n is 1, X is not a hydrogen atom; A is at least one group selected from a straight-chain or branched chain alkyl group, a cycloalkyl group, an aryl group and an aralkyl group; and Rs are each independently a group selected from a hydrogen atom and a hydrocarbon group of 1–6 carbon atoms, and the vinyl ether is a compound represented by the following general formula (2):

$$X-A \underset{\underset{H}{\overset{R}{\underset{|}{C}}}-\underset{H}{\overset{R}{\underset{|}{C}}}-OH)_{n-m}}{\overset{\overset{R}{\underset{|}{C}}=CH)_m}{\underset{|}{\overset{R}{\underset{|}{C}}}}} \quad (2)$$

wherein n, X, A and Rs have the same definitions as given in the general formula (1); and m is 1 or 2 with a proviso that when n is 1, m is 1.

6. The process according to claim 5, wherein the 2-hydroxyalkyl compound is a member selected from the group consisting of (a) diethylene glycol, (b) triethylene glycol, (c) diisopropylene glycol, (d) 2-(3-hydroxypropoxy) ethanol, (e) 2-(4-hydroxybutoxy) ethanol and (f) 2-(2-dimethylaminoethoxy)ethanol.

7. The process according to claim 6, wherein the corresponding vinyl ethers produced are (a') hydroxyethyl vinyl ether, (b') hydroxyethoxyethyl vinyl ether, (c') 1-(2-hydroxypropoxy)-1-propylene, (d') hydroxypropyl vinyl ether, (e') hydroxybutyl vinyl ether and (f') dimethylaminoethyl vinyl ether, respectively.

* * * * *